(12) United States Patent
Kurtz et al.

(10) Patent No.: US 6,446,510 B1
(45) Date of Patent: Sep. 10, 2002

(54) FORCE TRANSDUCER ASSEMBLY

(75) Inventors: Anthony D. Kurtz, Ridgewood; Robert Gardner, Westwood; Richard Martin, Ridgewood; Lou DeRosa, Wayne; Estelle Anselmo, Succasunna, all of NJ (US)

(73) Assignee: Kulite Semiconductor Products, Inc., Leonia, NJ (US)

( * ) Notice: Subject to any disclaimer, the term of this patent is extended or adjusted under 35 U.S.C. 154(b) by 0 days.

(21) Appl. No.: 09/624,084

(22) Filed: Jul. 24, 2000

(51) Int. Cl.[7] .............................. G01N 3/00; G01N 3/32
(52) U.S. Cl. .............................. 73/796; 73/760; 73/813; 73/794
(58) Field of Search .................. 73/796, 727, 862.046, 73/862.21, 862.27, 862.381, 794, 813

(56) References Cited

U.S. PATENT DOCUMENTS

| | | | | |
|---|---|---|---|---|
| 5,134,887 A | * | 8/1992 | Bell ........................... | 73/718 |
| 5,379,653 A | * | 1/1995 | Saner ........................ | 73/862.59 |
| 6,058,782 A | | 5/2000 | Kurtz et al. | |

* cited by examiner

Primary Examiner—Benjamin R. Fuller
Assistant Examiner—Andre Allen
(74) Attorney, Agent, or Firm—Duane Morris LLP

(57) ABSTRACT

A force transducer assembly for measuring compressive and tensile loads applied to a force transmission device, the assembly includes a housing, a sleeve assembly and a sensor device. The housing has a hollow interior. The sleeve assembly is coupled within the interior of the housing. The sensor device is secured within the interior of the housing between a portion of the sleeve assembly and a portion of the housing. The sensor device includes first and second sensors each including an isolation diaphragm at least partially defining an oil-filled cavity, and a piezoresistive sensor positioned so as to be effected by a change in pressure in the oil-filled cavity. When a first force is applied to the apparatus in a first direction via the force transmission device, one of the isolation diaphragms is deflectable in response thereto, and when a second force is applied in a second direction opposite to the first direction, the other of the isolation diaphragms is deflectable in response thereto. This causes a corresponding output from the sensor assembly. The first direction exerts a push on the device and the second direction exerts a pull on the device.

19 Claims, 7 Drawing Sheets

FORCE TRANSDUCER ASSEMBLY

FIELD OF INVENTION

The present invention relates generally to force measurement, and more particularly to a force transducer assembly which measures both tensile and compressive forces applied via a force transmission device and converts applied forces into pressures in two pressure sensing capsules.

BACKGROUND OF INVENTION

It is desirable to record whether a force transmission device, such as a connecting rod in a rudder control system of an airplane for example, is being subject to compressive or tensile loads, and to determine the magnitude of those applied loads. For force transmission devices of this type, such as linkages attached to a control wheel, control column, elevator control or rudder control pedal of an airplane for example, it is known to be desirable to measure what type and with what magnitude a force is being applied to it. In this way one can determine the direction a rudder or other device was moved in and the magnitude of a force applied. It is desirable to measure the forces being applied to these, as well as other types of transmission devices, so that appropriate data may be stored for later retrieval, e.g. in an airplane flight recorder. Such devices are frequently called "load cells" and most such devices usually transmit tensile or compressive applied forces to an internal load column which in turn is stressed in tension or compression. The resulting stress in the column gives rise to a strain in the column which is measured by affixing "strain gages" to the column and by connecting the "strain gages" into a Wheatstone Bridge which provides an output which is proportional to the strain and hence the applied load. Such a device is inherently costly because of the required close dimensional tolerances of the column and the exactness of the placement of the individual strain gages. In addition, it is also very labor intensive because each individual strain gage must be separately applied to the column and only then can the four strain gages be connected into a Wheatstone Bridge. Moreover, any difference in temperature across or along the column can result in error signals, since each strain gage can change its resistance because of a change in temperature.

Accordingly, it is an object of the present invention to provide a different way to sense the application of tensile and compressive forces by separately converting them into a pressure for each force. By using two pressure capsules, only one of which undergoes a pressure increase during a tensile load while the other capsule undergoes a pressure increase only during a compressive load, and by using a half-bridge sensor configuration from each sensor, an output proportional to the load can be obtained.

SUMMARY OF THE INVENTION

A force sensor assembly for measuring compressive and tensile loads applied to a force transmission device including first and second ends, the assembly including: a housing coupled to the first end of the force transmission device and defining an interior; a sleeve assembly coupled within the interior of the housing and to the second end of the force transmission device; and, a sensor device secured within the interior of the housing between a portion of the sleeve assembly and a portion of the housing, the sensor device including first and second sensor capsule, each capsule including an isolation diaphragm at least partially defining an oil-filled cavity and a piezoresistive sensor positioned so as to be effected by a change in pressure in the oil-filled cavity, whereby when a first force is applied to the apparatus via the force transmission device, one of the capsules is subjected to a pressure deflects and when a second force is applied, the other of the capsules is subjected to a pressure; each capsule containing a halfbridge and the two halfbridges interconnected to form a full bridge. Thus, the resulting full bridge will indicate either a tensile or a compressive force.

BRIEF DESCRIPTION OF THE FIGURES

The advantages and aspects of the present invention will be more fully understood in conjunction with the following detailed description and accompanying drawings, wherein.

DETAILED DESCRIPTION OF THE INVENTION

Figure 1:
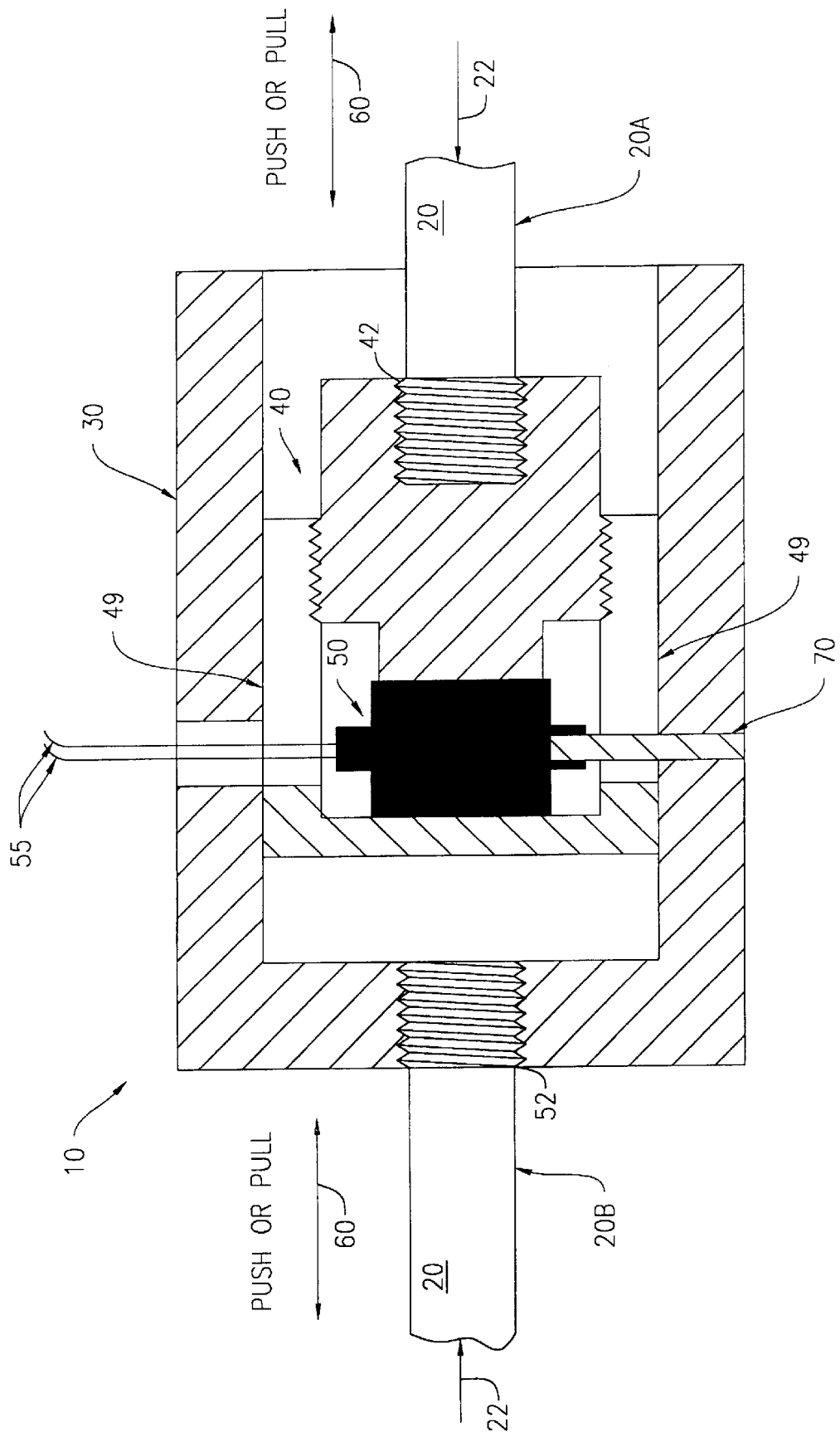
FIG. 1 illustrates a force sensor apparatus according to the present invention.

Referring now to the figures, like references identify like elements of the invention. FIG. 1 illustrates a force sensing apparatus 10 according to the present invention. The apparatus 10 generally includes outer housing 30, sleeve assembly 40 and sensor device 50. Sleeve assembly 40 includes a recess 42 for receiving an end 20A of a connecting rod 20, and outer housing 30 includes a recess 52 for receiving an end 20B of the connecting rod 20. Ends 20A and 20B of connecting rod 20 and recesses 42 and 52 are preferably threaded with a same thread pitch. Thus, when these threaded ends 20A and 20B are respectively coupled to the threaded recesses 42, 52 compressive and tensile loads can be transmitted to the apparatus 10 via the connecting rod 20. It should be understood that other suitable techniques for coupling the ends 20A and 20B of connecting rod 20 to sleeve assembly 40 and outer housing 30, respectively, could of course be used, the important feature being that either a compressive or tensile force 60 can be applied to the apparatus 10 by either end 20A or 20B of connecting rod 20. The sensor device 50 is preferably secured to the outer housing 30 via two pins 70 positioned $\alpha°$ apart from one another and both being perpendicular to longitudinal axis 22 of the connecting rod 20 and apparatus 10. Preferably $\alpha=120$, although any other suitable number can of course be utilized, as well as any number of pins.

Figure 2:
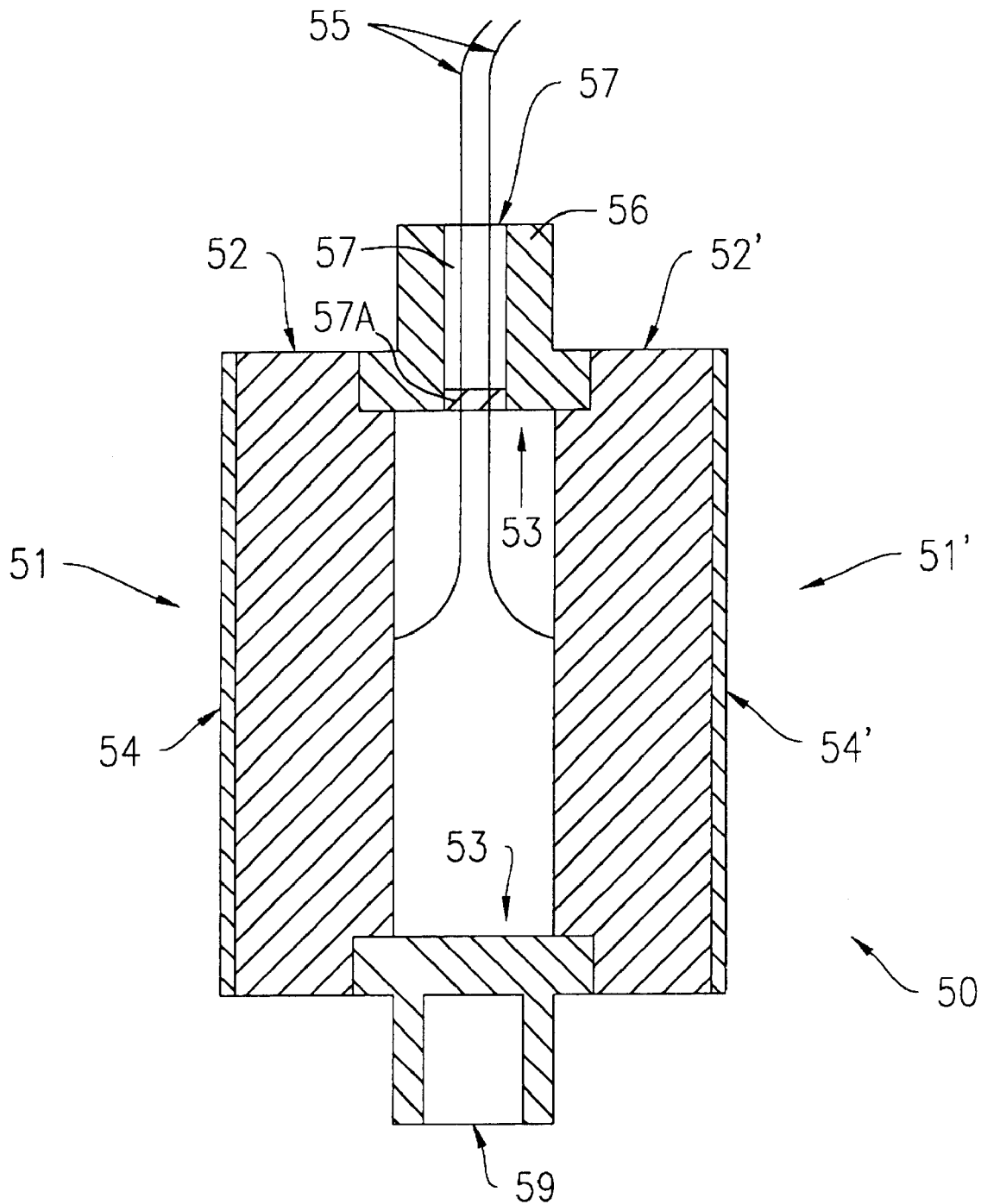
FIG. 2 illustrates a sensor device containing two capsules suitable for use in the assembly of FIG. 1.

Referring now also to FIG. 2, therein is illustrated an exemplary sensor device 50 suitable for use within the assembly 10 according to the present invention. The sensor device 50 includes two oil-filled sensors 52, 52', isolation diaphragms 54, 54' respectively secured over each sensor 52, 52' and electrical leads 55 coupled to sensors 52, 52'. The sensor device 50 preferably includes three apertures 53 about it periphery such that they are perpendicular to a longitudinal axis 51 of the sensor device 50 and positioned α° apart from one another. Within two of the apertures 53 are secured mounting portions 58 which each include a recess 59 suitable for receiving and securing there within one of the pins 70. Bushing 56 is preferably secured within the third aperture 53. Bushing 56 preferably includes a channel 57 passing there through and of sufficient dimensions to accommodate leads 55 and a hermetic header 57A.

Figure 3:
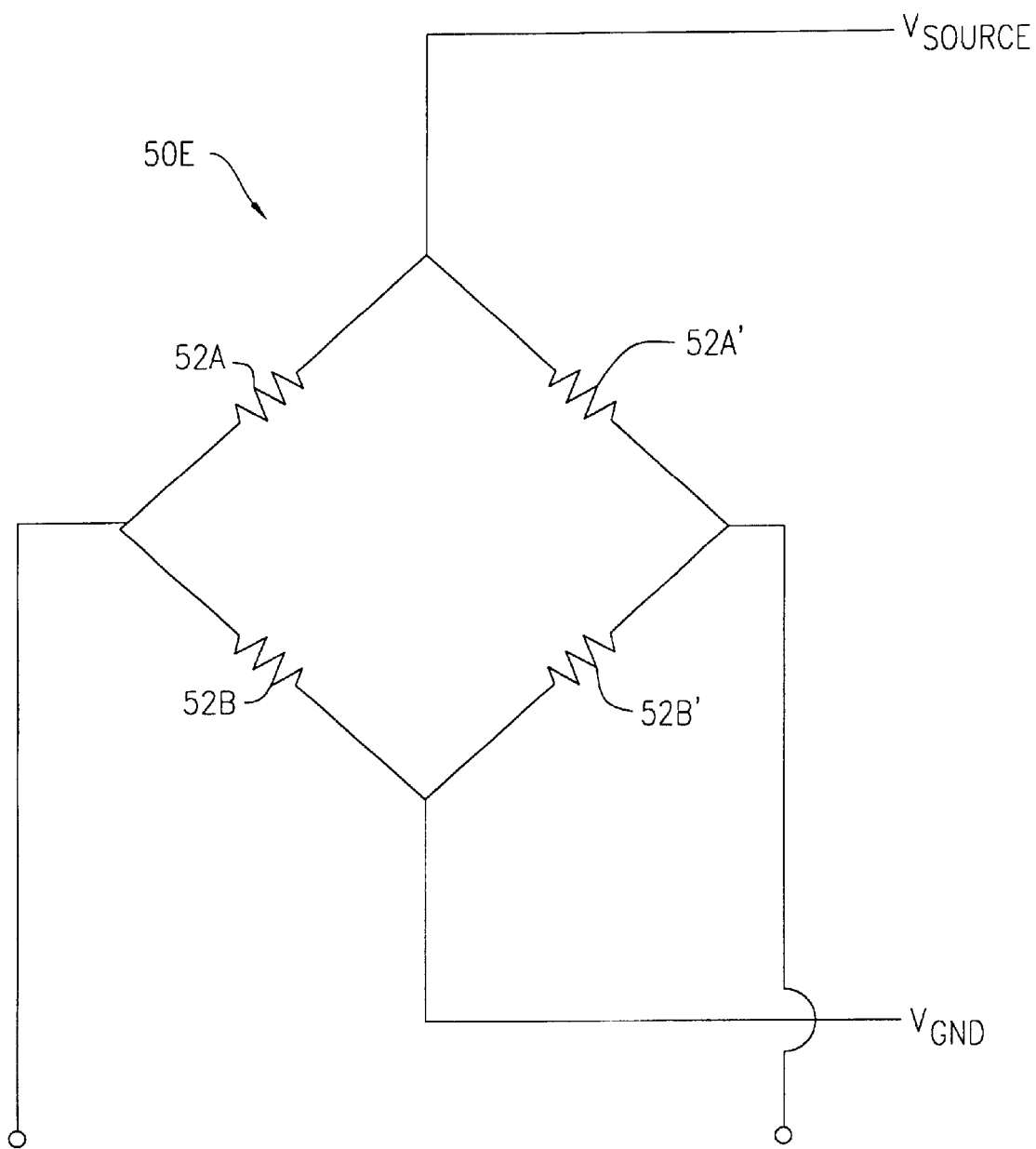
FIG. 3 illustrates an electrical representation of the sensor device of FIG. 2 showing individual half-bridge sensor configurations from each capsule connected to form a full Wheatstone bridge sensor configuration.

Referring now to FIG. 3, therein is illustrated an electrical representation 50E of the sensor device 50 of FIG. 2. The sensor 52 includes a piezoresistive half bridge configuration including piezoresistive devices 52A and 52B while the sensor 52' includes a piezoresistive half bridge configuration including two piezoresistive device 52A' and 52B'. The piezoresistive devices 52A, 52B, 52A', 52B' are coupled in a full Wheatstone bridge configuration which is electrically connected to leads 55. The operation of such half and full bridges is, of course, well known to those possessing an ordinary skill in the pertinent art.

Figure 4:
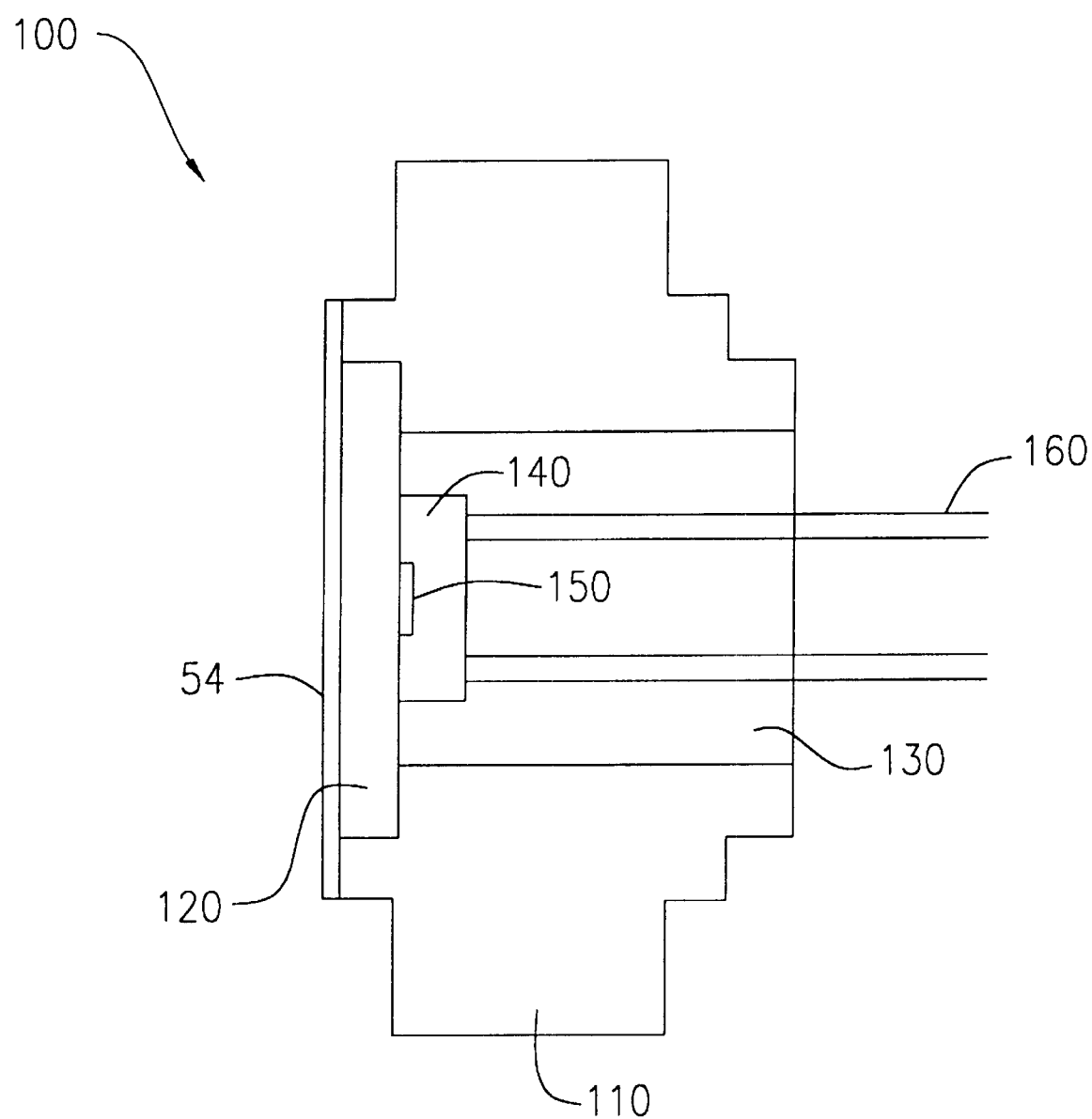
FIG. 4 illustrates a cross-section of a sensor suitable for use in the sensor device of FIG. 2.

Referring now also to FIG. 4, therein is illustrated a sensor 100 suitable for use as sensor 52 or 52' within the sensor device 50. The sensor 100 includes housing 110 having a cavity 120 being defined in combination with the isolation diaphragm secured there over, e.g. 54, 54'. The cavity 120 is preferably filled with a suitably non-compressible oil. A header 130 is secured within the housing 110. The header 130 has a ceramic portion 140 which abuts the cavity 120. Within the ceramic portion 140 is secured a chip 150 which includes a deflectable diaphragm having two piezoresistors formed thereon in a ½ grid configuration as has been discussed with regards to FIG. 3, e.g. 52A and 52B or 52A' and 52B', and electrical interconnections thereto. The chip 150 can be formed in accordance with the teachings of commonly assigned U.S. Pat. No. 6,058,782, entitled HERMETICALLY SEALED ULTRA HIGH TEMPERATURE SILICON CARBIDE PRESSURE TRANSDUCERS AND METHOD FOR FABRICATING SAME, issued on May 9, 2000, the entire disclosure of which is hereby incorporated by reference as if being set forth in its entirety herein. Of course, any other suitable method or chip design could alternatively be utilized. Basically, according to the preferred form of the present invention, each chip includes a plurality of piezoresistors formed on a deflectable diaphragm in a half bridge configuration.

Figure 5:
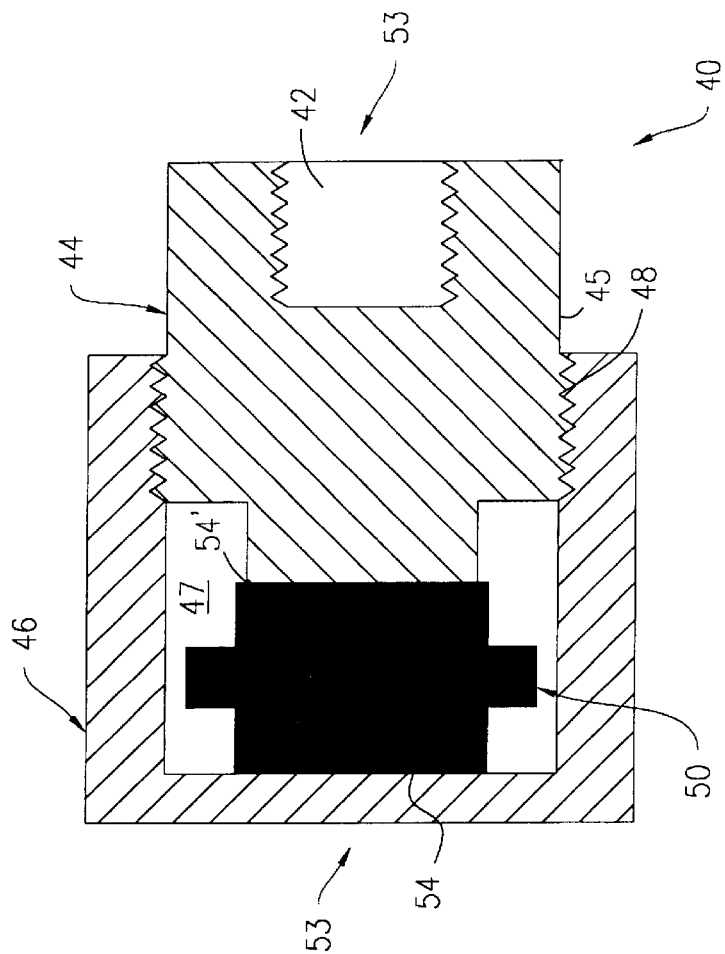
FIG. 5 illustrates the sleeve assembly of FIG. 1.

Referring now also to FIG. 5 therein is illustrated the sleeve assembly 40 of FIG. 1 and sensor device 50 of FIG. 2. The sleeve assembly 40 includes inner sleeve 44 and outer sleeve 46 securing sensor device 50 within a cavity 47 of outer sleeve 46. The inner sleeve 44 includes a threaded outer peripheral portion 45 having a same pitch as a threaded interior surface portion 48 of the outer sleeve 46. The sensor is positioned within the cavity 47 such that when the portions 45, 48 of the inner and outer sleeves 44, 46 are threaded together, the inner sleeve 44 abuts isolation diaphragm 54' of the sensor device 50 and outer sleeve 46 abuts isolation diaphragm 54. Of course, other suitable methods for securing the outer sleeve 46 to the inner sleeve 44 can be used. Preferably the inner sleeve 44 is threaded into the outer sleeve 46 such that just enough pressure is exerted upon the diaphragms 54, 54' to secure the device 50 within the cavity 47. The inner sleeve 44 includes the recess 42 formed in an oppositely disposed longitudinal end from that of the inner sleeve 44 which abuts the isolation diaphragm 54'.

Figure 6:
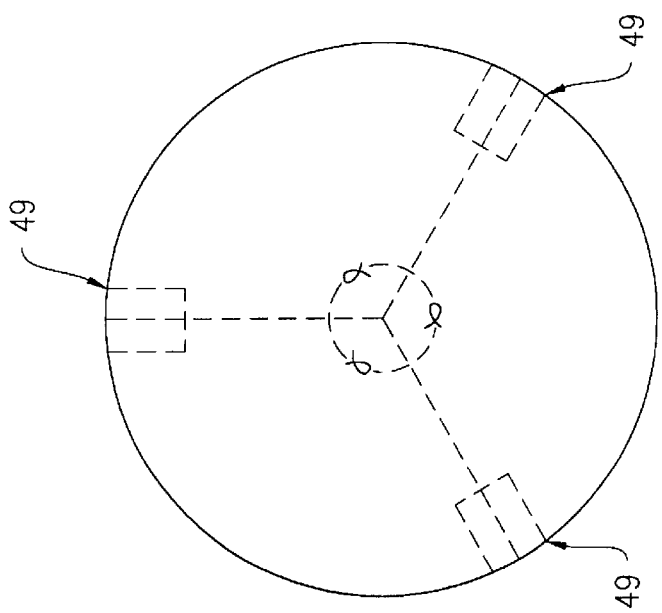
FIG. 6 is an end-view of the sleeve assembly of FIG. 5.

Referring now also to FIG. 6, therein is illustrated an end view of the outer sleeve 46. Outer sleeve 46 includes slots 49 there through which run parallel to the longitudinal axis 53 of the sleeve assembly 40. The outer sleeve 46 preferably includes three slots 49 positioned α° with respect to one another and of suitable dimensions to accommodate one of the pins 70 passing there through.

Referring again to FIGS. 1 and 2 as well, each of the pins 70 passes through one of the slots 49 and is secured within the recess 59 of one of the mounting portions 58. The leads 55 pass through the bushing 56 and then to a hermetic header 57A from which additional leads pass through the third slot 49.

Figure 7:
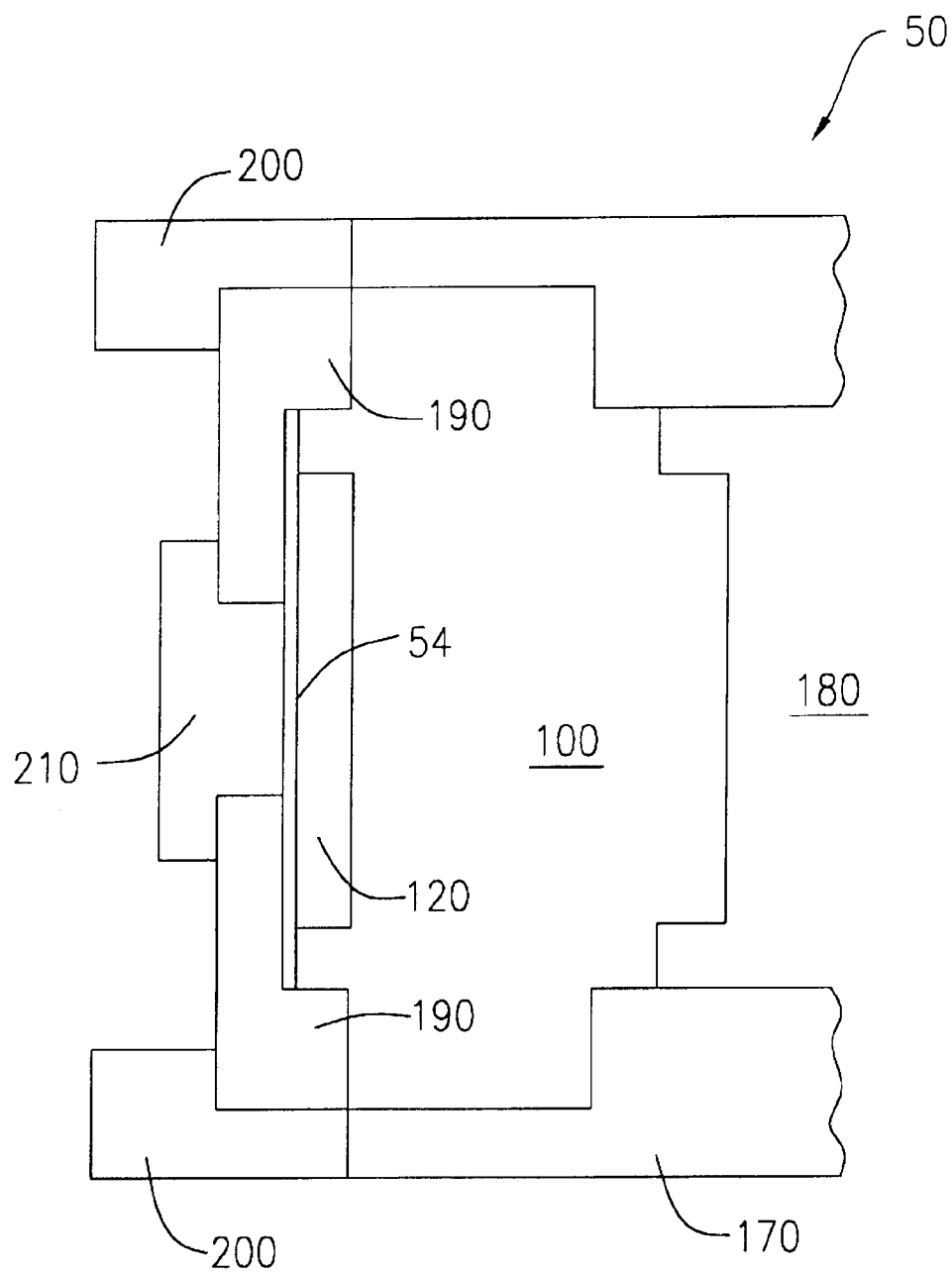
FIG. 7 illustrates an enlarged view of a particularly preferred form for mounting the sensor of FIG. 4 to form one sensor device of FIG. 2; and, FIGS. 8A and 8B illustrate operational aspects of the apparatus of FIG. 1 under compressive and tensile loads, respectively.

Referring now to FIG. 7, therein is illustrated a particularly preferred form for mounting the sensor of FIG. 4 to form the sensor device of FIG. 2. The sensor device 50 preferably includes a substantially cylindrical sensor device housing 170 forming an internal hollow 180 having two open ends. The sensor 100 is secured within the hollow 180 such that the diaphragm 54 is accessible through one of the open ends of the housing 170 and a like sensor can be secured such that its diaphragm 54 is accessible via the other open end. An elastomeric member 190 having a central aperture there through is secured over the diaphragm 54 using covering cap member 200 which also has a central aperture. A force collector 210 is positioned within the aperture of the elastomeric member 190 so as to abut the diaphragm 54. Thus, using well known principles, a force applied to the collector 210 is applied to the diaphragm 54 which creates a pressure within the oil cavity 120.

Figure 8A:
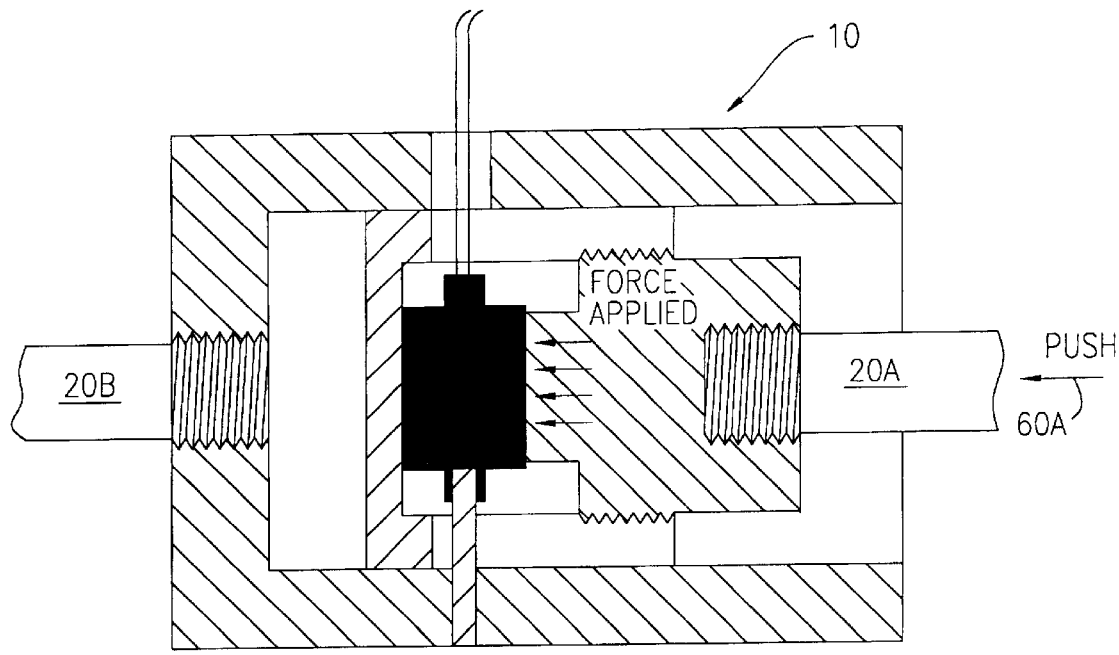
Figure 8B:
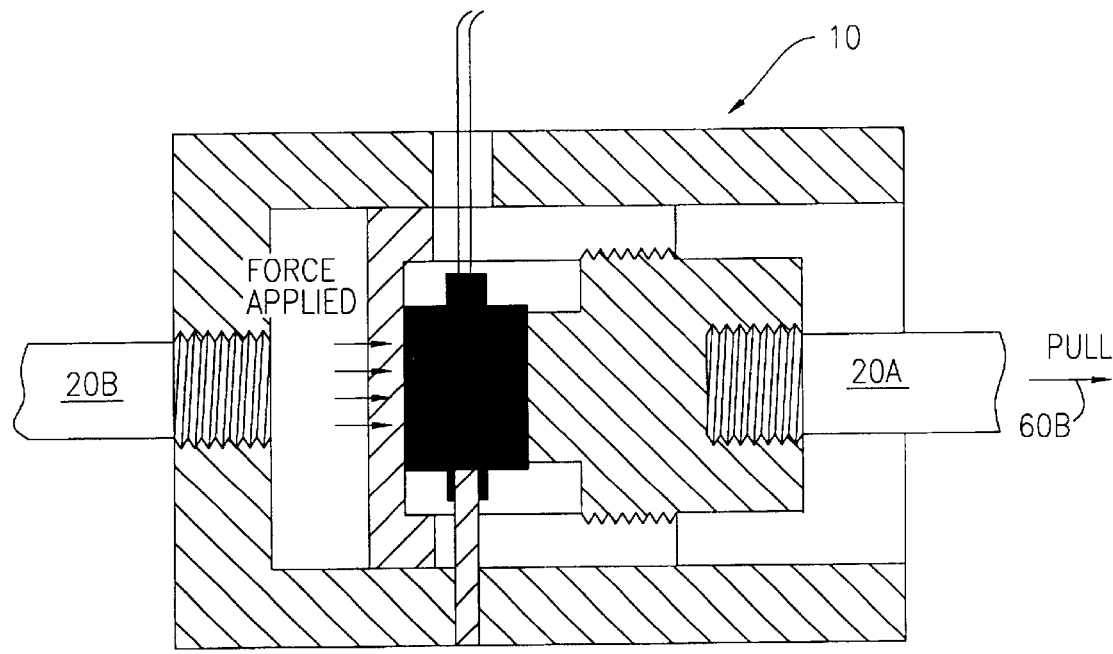

Referring now to FIGS. 8A and 8B, when a compressive force 60A is applied to the apparatus 10 via the end 20A of connecting rod 20 a corresponding force is applied to the isolation diaphragm 54' causing an electrical signal which is indicative of the compressive force 60A to be output via the leads 55. When a tensile force 60B is applied to the apparatus 10 via the end 20A of the connecting rod 20 a corresponding force is applied to the isolation diaphragm 54 causing an electrical signal which is indicative of the tensile force 60B to be output via the leads 55.

Although the invention has been described and pictured in a preferred form with a certain degree of particularity, it is understood that the present disclosure of the preferred form, has been made only by way of example, and that numerous changes in the details of construction and combination and arrangement of parts may be made without departing from the spirit and scope of the invention as hereinafter claimed. It is intended that the patent shall cover by suitable expression in the appended claims, whatever features of patentable novelty exist in the invention disclosed.

We claims:

1. A force transducer apparatus for measuring compressive and tensile loads applied to a force transmission device, said apparatus comprising:

a housing having a hollow interior;

a sleeve assembly disposed within said interior of said housing; and, a sensor device secured within said interior of said housing between first and second portions of said sleeve assembly, said sensor device including first and second sensors each including an isolation diaphragm at least partially defining an oil-filled cavity and a piezoresistive sensor positioned adjacent the cavity so as to be effected by a change in pressure in said oil-filled cavity;

wherein a push force applied to said first portion of said sleeve assembly by said force transmission device causes said first portion of said sleeve assembly to deflect said isolation diaphragm of said first sensor thereby causing said sensor device to output a signal indicative of said push force, and a pull force applied to said first portion of said sleeve assembly by said force transmission device causes said second portion of said sleeve assembly to deflect said isolation diaphragm of said second sensor thereby causing said sensor device to output a signal indicative of said pull force.

2. The apparatus of claim 1, wherein said housing includes a recess for receiving said first end of said force transmission device.

3. The apparatus of claim 2, wherein said sleeve assembly includes a recess for receiving said second end of said force transmission device.

4. The apparatus of claim 3, wherein said recesses are threaded with a substantially identical pitch, and said first and second ends of said force transmission device are respectively threaded there into.

5. The apparatus of claim 1, wherein said sensor device is coupled to said housing using a plurality of pins.

6. The apparatus of claim 5, wherein said sleeve assembly includes a plurality of slots.

7. The apparatus of claim 6, wherein each of said pins passes through one of said slots.

8. The apparatus of claim 7, further comprising a plurality of electrical interconnections coupled to said piezoresistive sensors.

9. The apparatus of claim 7, wherein each of said piezoresistive sensors includes a plurality of piezoresistors coupled in a half Wheatstone bridge configuration and said interconnections are coupled to said piezoresistive sensors so as to form a full Wheatstone bridge configuration from said half bridge configurations.

10. The apparatus of claim 9, wherein said interconnections pass through one of said slots.

11. The apparatus of claim 10, wherein said slots are separated by approximately 120° from one another with respect to a longitudinal axis of said sleeve assembly.

12. The apparatus of claim 8, wherein said force transmission device is a linkage in an aircraft control system.

13. The apparatus of claim 12, wherein said electrical interconnections are provide signals to a flight recorder system.

14. A force measuring device suitable for placement within a connecting rod having a break therein which defines first and second ends of said connecting rod, sad device comprising:

a housing including an interior chamber defined by a side wall and a closed end;

a sleeve assembly disposed within said housing and including a recess for securing one of said first and second ends of said connecting rod therein; and, a sensor assembly disposed within said chamber and coupled to said side wall of said housing, said sensor assembly including a plurality of sensors positioned therein;

wherein, a first of said sensors is positioned to measure a push force applied to said sleeve assembly by said connecting rod, and a second of said sensors is positioned to measure a pull force applied to said sleeve assembly by said connecting rod.

15. The apparatus of claim 1, wherein said sensor assembly is coupled to said housing using a plurality of pins.

16. The apparatus of claim 5, wherein said sleeve assembly includes a plurality of slots and each of said pins passes through one of said slots.

17. The device of claim 16, wherein each of said sensors includes a plurality of piezoresistors coupled in a half Wheatstone bridge configuration and said sensors are electrically interconnected to form a full Wheatstone bridge configuration from said half bridge configurations.

18. The apparatus of claim 16, further comprising a plurality of electrical leads coupled to said full Wheatstone Bridge configuration to provide signals to a flight recorder system.

19. The apparatus of claim 1, wherein a push force applied to said housing via said force transmission device causes said second portion of said sleeve assembly to deflect said isolation diaphragm of said second sensor thereby causing said sensor device to output a signal indicative of said push force, and a pull force applied to said housing via said force transmission device causes said first portion of said sleeve assembly to deflect said isolation diaphragm of said first sensor thereby causing said sensor device to output a signal indicative of said pull force.

* * * * *